United States Patent

Serra-Tosio et al.

[11] Patent Number: 5,271,279
[45] Date of Patent: Dec. 21, 1993

[54] APPARATUS FOR MEASURING THE ELONGATION OF SAMPLE STRIPS

[75] Inventors: Jean-Marie Serra-Tosio, Meylan; Yves Chave, Gieres, both of France

[73] Assignee: Francaise de Papeterie et de l'Imprimerie, Paris, France

[21] Appl. No.: 865,615

[22] Filed: Apr. 9, 1992

[30] Foreign Application Priority Data

Apr. 10, 1991 [FR] France ................ 91 04664

[51] Int. Cl.⁵ .............................................. G01N 3/08
[52] U.S. Cl. .......................................... 73/833; 73/856
[58] Field of Search ............. 73/831, 833, 826, 856, 73/828

[56] References Cited

U.S. PATENT DOCUMENTS 4,513,611 4/1985 Bohlin .
4,998,825 3/1991 Hublikar et al. ................... 73/826 X

FOREIGN PATENT DOCUMENTS

2943691 3/1981 Fed. Rep. of Germany .
1273353 5/1957 France .

Primary Examiner—Jerry W. Myracle
Attorney, Agent, or Firm—Lowe, Price, LeBlanc & Becker

[57] ABSTRACT

An apparatus for measuring the respective elongations of several sample strips (13), comprises: a vertical frame (51) provided with a fixed upper gripping jaw (27) and a mobile lower gripping jaw (15) to maintain each of the strips (13), the lower gripping jaw (15) stretches the strip by gravity effect; and an electronic displacement sensor (33, 35) associated to each lower gripping jaw (15). Each gripping jaw comprises a sole and a plate articulated on the sole. A magnet (11) is mounted in the sole, flush with a contact surface of the sole, for urging the plate against the contact surface by magnetic attraction.

9 Claims, 6 Drawing Sheets

Fig. 5

APPARATUS FOR MEASURING THE ELONGATION OF SAMPLE STRIPS

BACKGROUND OF THE INVENTION

The present invention relates to an apparatus for measuring the elongation of paper strips placed in an atmosphere, the humidity and temperature of which is controlled.

One of the characteristics of paper is its dilatation as a function of air humidity, at a constant temperature. To measure this characteristic, there exists apparatuses in which is disposed a series of sample strips of paper. These sample strips are subject, in an air-tight chamber, to different predetermined humidity atmospheres and their length variations are measured. The conventional apparatuses for measuring the elongation of strips comprise, for each strip, an upper and a lower gripping jaw in which the extremities of the strip are held. Each upper or lower gripping jaw is coupled to a displacement measuring instrument and to a zero setting device for the measuring instrument.

In an apparatus of the "Neenah" type available from Technidyne, measurement is made by micrometers coupled to the upper gripping jaws, and having rollers accessible from the top of the apparatus. The lower jaws are coupled to articulated levers, the horizontal position of which is visually controlled by water levels. Initially, the roller of each micrometer is activated to vertically move the associated strip until the horizontal position of the corresponding lever is obtained, which is shown by the centering of the associated level bubble. To measure the length variations, the roller of each micrometer is activated again to render the levers horizontal and the elongation is then calculated from the roller rotation.

In an apparatus of the 68936 type available from Sodexim S.A., the length is measured by comparators measuring the position of the lower gripping jaws. Initially, each comparator is reset by vertically moving the associated strip by means of a screw coupled to the upper gripping jaw and accessible from the top of the apparatus. Elongations can then be directly read on the comparators.

In the known apparatuses, it is therefore necessary, for each strip, to set the zero of an associated measurement instrument and to note down measurement, either manually (micrometer) or visually (comparator), which is tedious if there is a large number of strips. Moreover, the conventional gripping jaws have various drawbacks.

A first known type of gripping jaw is a spring clip. The spring clip can be easily handled, but does not generally enable to uniformly press paper strips. As a result, the paper strip can slide obliquely while it is being positioned or afterwards. To avoid this drawback, the spring of the clip can be stiffened, but the use of these clips is then more unpleasant, especially if there is a high number of clips, because substantial efforts are necessary to open them.

A second known more reliable type of gripping jaw comprises an eccentric pressing on a metal sheet while tightening the strip between this metal sheet and a support. However, such a gripping jaw does not allow satisfactory tightening of too thin or too thick strips. Moreover, the tightening effort is rather high and the tightening movement is not easy, which renders the use of these gripping jaws unpleasant if they are numerous.

Magnetic gripping jaws are also known, such as those described in patent DE-B-29 43 691, used to fix square sheets on a vertical plane.

SUMMARY OF THE INVENTION

An object of the invention is to provide a new apparatus for measuring the elongation of sample strips in which the insertion of sample strips in the gripping jaws is particularly easy.

Another object of the invention is to provide a new apparatus for measuring the elongation of sample strips that do not require several resets of the measurement instruments.

A further object of the invention is to provide a guiding means of the lower gripping jaw for further simplifying the insertion of the sample strips.

The invention provides an apparatus for measuring the respective elongations of several sample strips, comprising a base, a vertical frame, and for each strip: a fixed upper gripping jaw for tightening the upper end of the strip, a mobile lower gripping jaw for tightening the lower end of the strip and to stretch it by gravity; and a displacement sensor for the lower gripping jaw. The gripping jaws are magnetic jaws, each of which comprises a sole and an articulated plate on the sole, a magnet being mounted in the sole to urge the plate against the sole by magnetic attraction; the soles of the lower gripping jaws being guided vertically with respect to the frame.

According to an embodiment of the invention, the sole of each lower gripping jaw is made of a non-magnetic material, and the jaw is guided by a groove made in a ferromagnetic part integral with the frame, the jaw being maintained guided in the groove only by its magnetic attraction.

According to an embodiment of the invention, each lower gripping jaw is coupled to the associated displacement sensor by means of a magnetic gripping device.

According to an embodiment of the invention, each gripping jaw comprises an articulated plate on the sole having a clearance perpendicular to the contact surface.

According to an embodiment of the invention, the sole of each gripping jaw comprises lateral walls serving to guide the paper strip to be tightened.

According to an embodiment of the invention, the displacement sensors are solenoid plunger sensors with a differential transformer, the solenoid plungers being coupled to the associated lower gripping jaws.

According to an embodiment of the invention, the apparatus comprises means to increase the elongation of each strip by adding loads on the lower gripping jaws.

According to an embodiment of the invention, the displacement sensors are fixed to the body and the apparatus comprises means for positioning the frame to high and low positions with respect to the body.

According to an embodiment of the invention, the apparatus comprises a horizontal ruler disposed between the upper and lower gripping jaws, the ruler having a lateral position where the lower gripping jaws freely slide in the vertical direction and another position where the lower gripping jaws abut against the ruler.

BRIEF DESCRIPTION OF THE DRAWINGS

The foregoing and other objects, features and advantages of the invention will be apparent from the following detailed description of preferred embodiments as illustrated in the accompanying figures wherein.

In the figures, same references designate same elements or equivalent elements.

DETAILED DESCRIPTION OF THE INVENTION

Figure 1A:
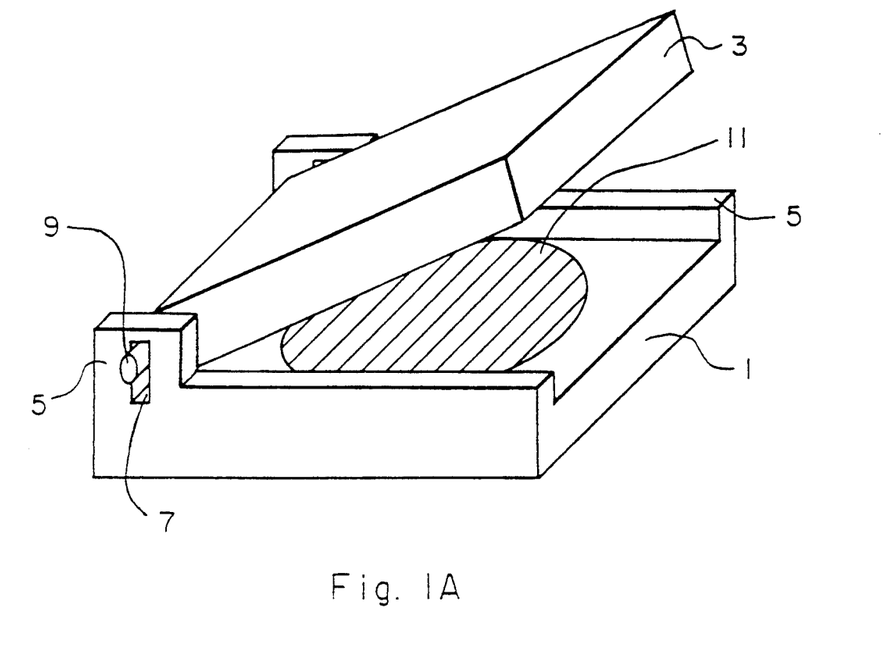
FIGS. 1A and 1B respectively show a simplified perspective view and a section view of a gripping jaw used according to the invention.

FIG. 1A is a perspective view of a simplified embodiment of a gripping jaw used according to the invention. The gripping jaw comprises a sole 1 made of a non-magnetic material on which is articulated a plate 3 abutting along a plane against the upper surface of the sole. Sole 1 comprises lateral rising walls 5 which laterally maintain plate 3. The lateral walls 5 comprise at the front part vertical grooves 7 in which are accommodated axes 9, laterally fixed to an end of plate 3. A permanent magnet 11 is mounted in a recess of sole 1 and is flush with the upper sole surface. Plate 3 is made of a ferromagnetic material and can therefore be urged against magnet 11 while ensuring satisfactory grip of a flat object placed between plate 3 and sole 1.

Figure 1B:
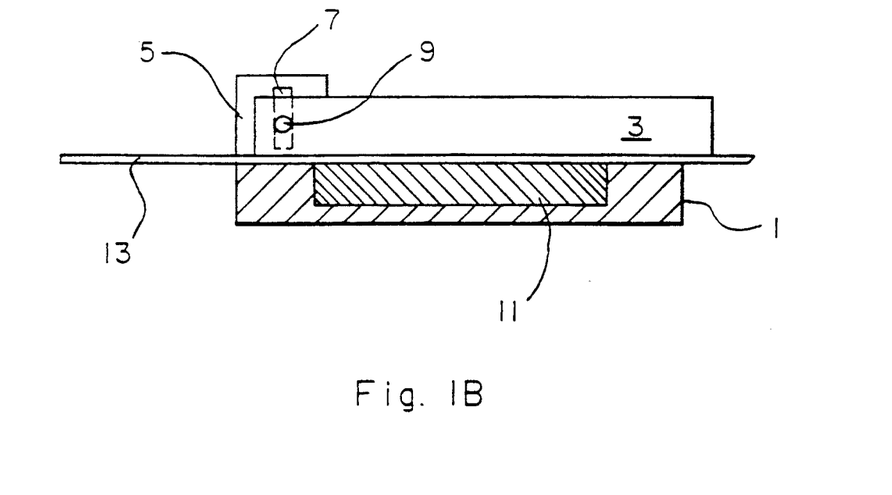

FIG. 1B is a side section view of the gripping jaw of FIG. 1, in closed position. As shown, a paper strip 13 is pressed between plate 3 and the upper surface of sole 1. The lateral positioning or guiding of the strip is ensured by the lateral walls 5.

It will be noted that the gripping jaw is adapted to receive paper strips of various thicknesses while maintaining the strips along a plane. In fact, according to the thickness of the strip, axis 9 will move more or less upwardly in groove 7, plate 3 remaining parallel with the upper surface of sole 1. In order to efficiently maintain strip 13 when its thickness is very significant, the contacting surfaces of plate 3 and sole 1 can be transversely scratched, roughened, or coated with an adhesive material. Also, one of the contacting surfaces can be provided with notches in register with holes in the other contacting surface.

Figure 2A:
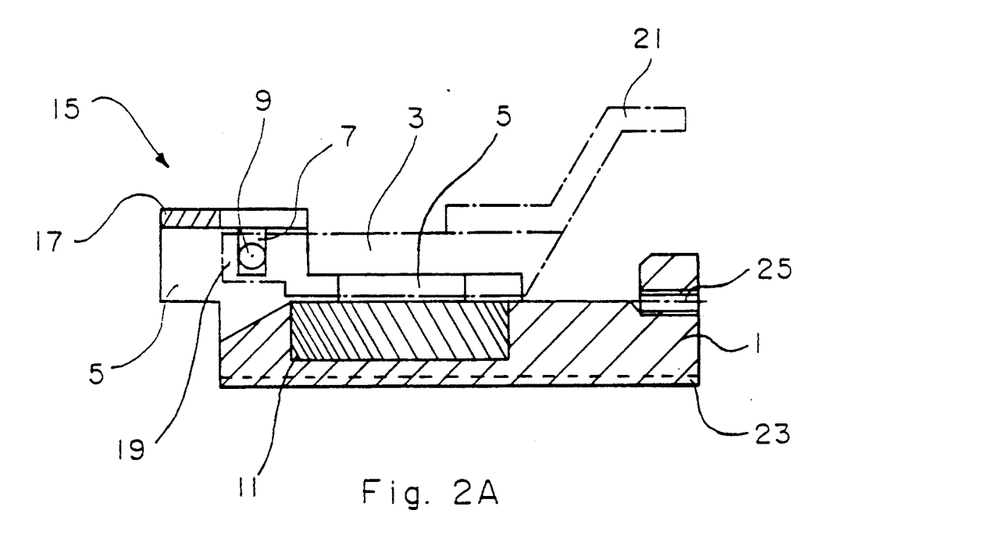
FIGS. 2A and 2B respectively show a side view and a top view of a preferred embodiment of a gripping jaw used according to the invention.
Figure 2B:
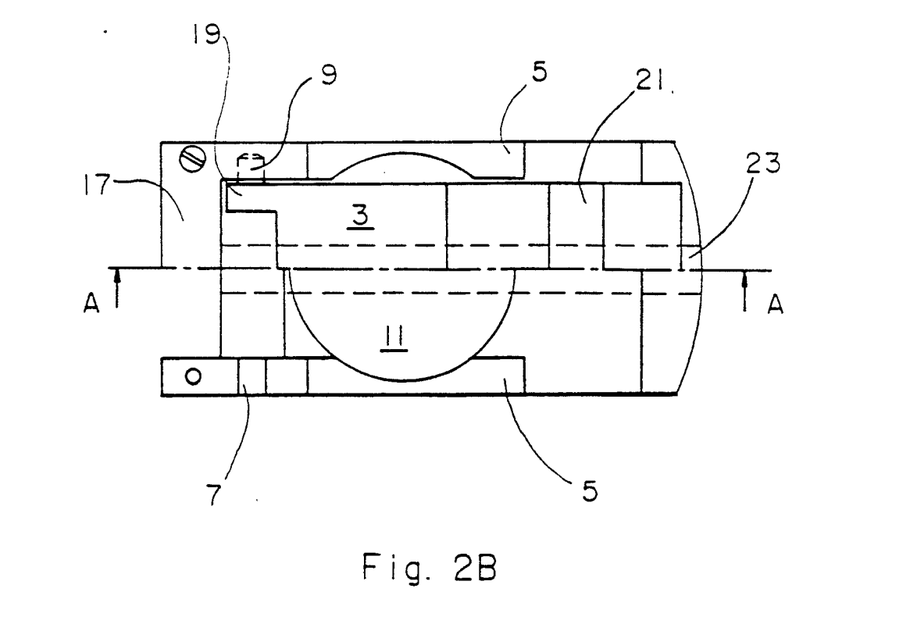

FIGS. 2A and 2B are two different views of a preferred embodiment of a lower gripping jaw used according to the invention and comprising the same elements as the gripping jaw of FIGS. 1A and 1B. FIG. 2A shows a side section view of the gripping jaw along an axis A—A. FIG. 2B represents the gripping jaw as two half top views, a half view representing the whole gripping jaw and the other half view representing the bare gripping jaw. Plate 3 is shown in dot-and-dash lines in FIG. 2A.

Grooves 7 end at the upper portion of the lateral walls 5 and are covered with a plate 17 screwed on the lateral walls. Plate 17 is cut curvely, as shown in FIG. 2B, to enable plate 3 to stand up to a position approximately perpendicular to sole 1. Axes 9 are pressed on or glued in lateral eyelets 19 longitudinally extending plate 3. In order to facilitate handling of the gripping jaw, plate 3 is provided at its back with a rising tongue 21.

Sole 1 comprises at its lower portion a longitudinal rib 23 for guiding the gripping jaw, as seen subsequently, along a groove in a part made of a ferromagnetic material. The gripping jaw being intended to vertically slide, rib 23 has to be maintained in the groove. To achieve this purpose, the bottom of magnet 11 is sufficiently close to the lower portion of sole 1 so that there is a slight magnetic attraction between magnet 11 and the part comprising the groove. Thus, one obtains a particularly simple means for maintaining the gripping jaw in the groove while allowing easy sliding.

The rear surface of sole 1 is provided with a thickened rising portion comprising a longitudinal inside thread 25 intended, as will be seen later in a specific application, to connect the gripping jaw to a displacement sensor.

Such gripping jaws are particularly simple to handle. They ensure positioning and guiding of a strip-shaped object. A strip can be introduced into the gripping jaw from both sides. The magnet ensures a double function, namely to tighten the strip and to maintain the gripping jaw in abutment against a support made of a ferromagnetic material.

Figure 3A:
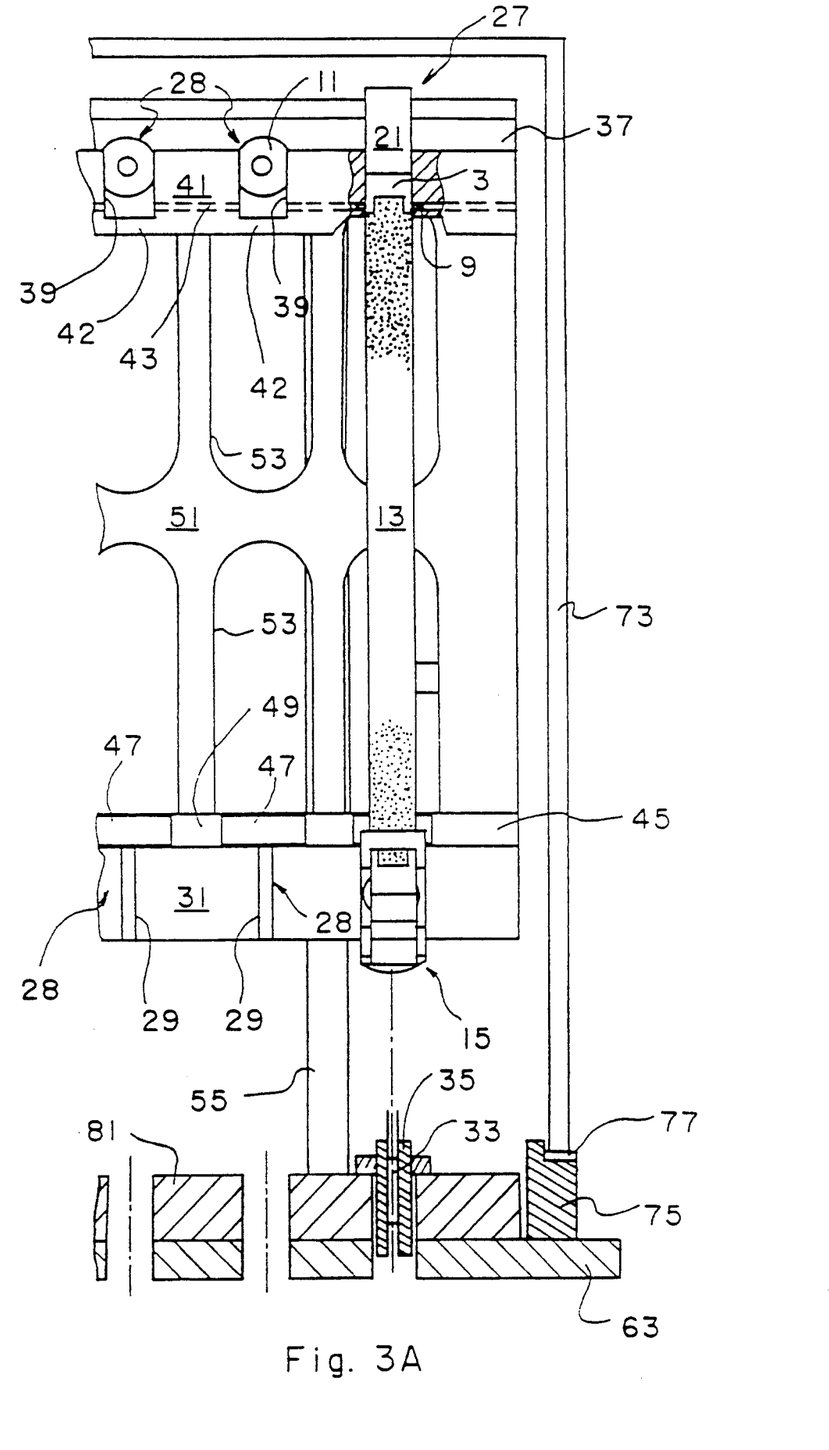
FIGS. 3A and 3B respectively show a front view and a side view of an embodiment of an apparatus for measuring the elongation of sample strips according to the invention.
Figure 3B:
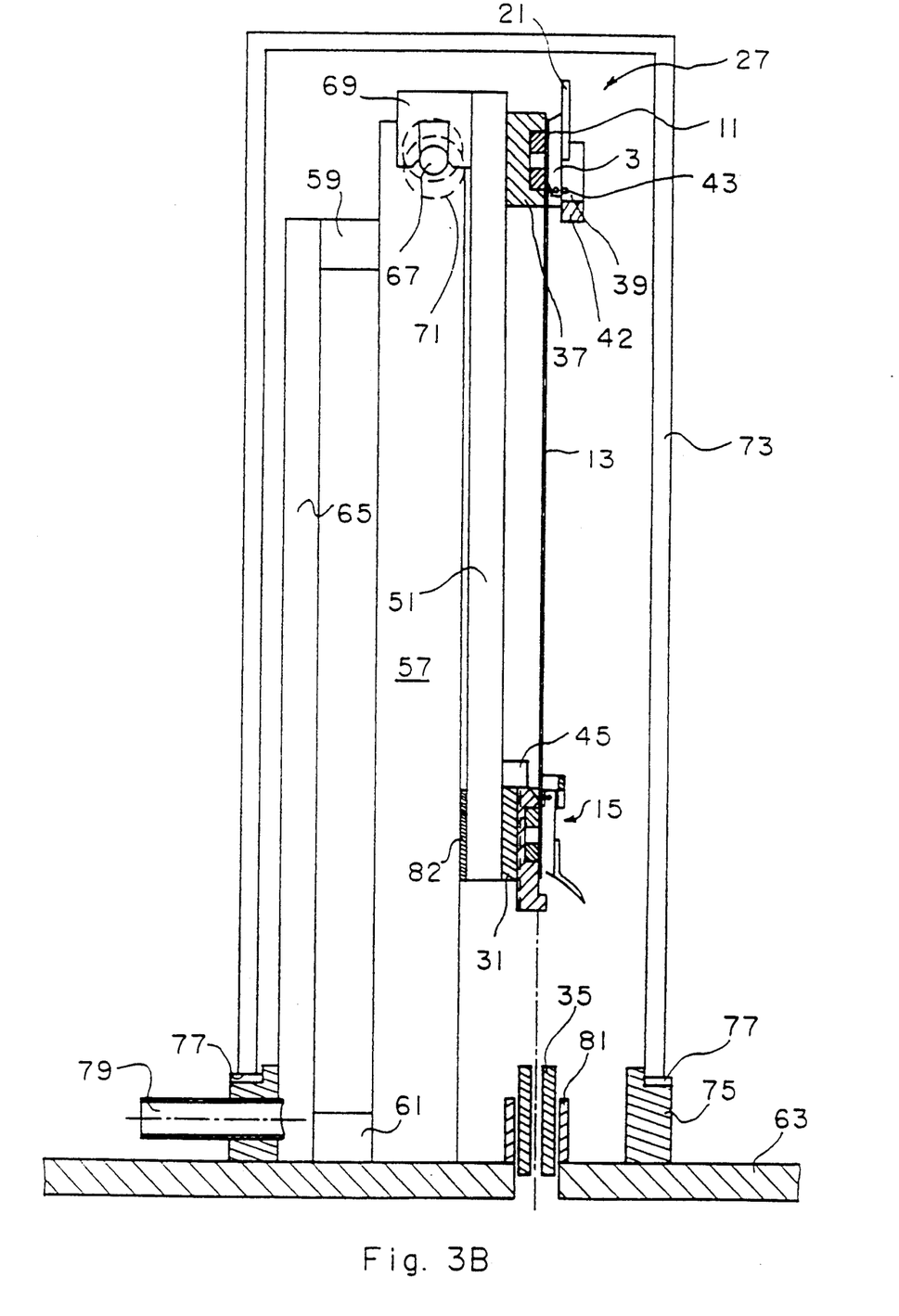

FIGS. 3A and 3B respectively show a front view and side view of an embodiment of an apparatus according to the invention. Some elements are represented by section or cut-away views to better illustrate their constitution. The apparatus is intended to measure the elongations of a series of sample strips, each vertically hooked between an upper gripping jaw and a lower gripping jaw and subject to a conditioned atmosphere, such as air at a controlled humidity and temperature. This apparatus comprises, as will be seen later on, various original and inventive aspects other than the use of the above described gripping jaws.

FIGS. 3A and 3B show a single strip 13 maintained at its extremities by a lower gripping jaw 15 and an upper gripping jaw 27. Four additional positions 28 of the upper and lower gripping jaws are represented.

The lower gripping jaws 15 are provided with ribs, such as above-described ribs 23, which slide along vertical grooves 29 of a fixed lower horizontal ruler 31 made of a ferromagnetic material. Each gripping jaw 15 is connected to a mobile element 33 of a displacement sensor 35 by means of a magnetic gripping device, described later on. Preferably, the displacement sensor 35 is an electronic sensor such as a solenoid plunger sensor 33, with a differential transformer, available from Sensorex.

The upper gripping jaws 27 are fixed and analogous to the lower gripping jaws 15 except that, as will be described hereafter, they have a common sole. The sole is replaced with an upper horizontal ruler 37 in which are longitudinally mounted magnets 11 appearing at the front surface of the ruler. The guiding lateral walls 5 are replaced with vertical grooves 39 of a horizontal ruler 41 screwed on ruler 37. Grooves 39 let appear each magnet 11 of ruler 37 and each groove is stopped at its lower extremity by a tie plate 42 of ruler 41. As represented in FIG. 3B, this tie plate 42 does not entirely close the extremity of groove 39 in order to enable strip 13 to pass downwardly. Each groove 39 receives a gripping jaw plate 3, with tongue 21 upward and articulation axis 9 downward. The articulation axes 9 are accommodated in a horizontal groove 43 of ruler 41, facing ruler 37 and ending in the lateral walls of grooves 39 near tie plates 42.

Handling of the upper gripping jaws 27 is particularly easy. When opening them, plates 3 abut against tie plates 42 and the operator has his hands free to insert the strip.

Contacting the upper portion of ruler 31 associated with the lower gripping jaws, is disposed a ruler 45 which slides laterally. Ruler 45 comprises on its front surface vertical grooves 47, broader than the lower gripping jaws. In the position of ruler 45 shown in FIG. 3A, the lower gripping jaws 15 can freely slide vertically along grooves 47. This ruler is useful to adjust the initial length of the sample strips.

The adjustment of the length of the strips is made when the latter are inserted. The insertion and adjustment of the strips are particularly easy. One inserts an extremity of a strip into an upper gripping jaw 27; ruler 45 is made to slide laterally so that a solid portion 49 thereof faces a groove 29; the other extremity of the strip is inserted into a lower gripping jaw 15 below ruler 45, the lower gripping jaw will then be self-adjusted and pressed thanks to its magnet into groove 29; one opens the upper gripping jaw 27 and lowers the strip until the lower gripping jaw 15 connects its displacement sensor by means of the magnetic gripping device, described later on; the strip is upwardly drawn until gripping jaw 15 abuts against the solid portion 49 of ruler 45; one closes the upper gripping jaw, and makes ruler 45 slide to its initial position, as shown. The lower gripping jaws can then freely move upwardly or downwardly.

Rulers 31, 37 and 45 are mounted on a frame 51. The upper ruler 37 can be screwed on frame 51 to several vertical positions, according to the desired strip length. Frame 51 is movable, which permits providing a second identical frame that can be fitted beforehand with a series of sample strips while measurements are being made with the first frame. For a better flow of atmosphere at strips 13, slots 53 are provided in the frame at the position of each strip 13, but the frame can also be formed by a rigid frame.

The frame is mounted on a base, a lateral post 55 of which is shown in FIG. 3A and another lateral post 57 in FIG. 3B. The lateral posts 55 and 57 are screwed on an upper spacer 59 and on a lower spacer 61, in turn screwed on a horizontal base 63. In order to ensure a better stiffness of the frame, a post 65 is screwed off-center to the back on spacers 59 and 61. The upper portions of posts 55 and 57 are crossed by an axis 67. On the upper portion of frame 51 are mounted lateral supports 69, one of which is shown in FIG. 3B, which support frame 51 and lay on eccentrics 71 fixed on the extremities of axis 67. The supports are arranged, as represented, so that frame 51 can be separated from the base by raising the frame.

The eccentric 71 shown in FIG. 3B is drawn in dotted lines in its extreme positions. With eccentrics 71, it is possible to set the frame 51 to a low position or to a high position, for reasons that will be seen later on.

All the elements that have been described are placed in an air-tight chamber enclosed inside a hood 73, preferably transparent, posed on a seat 75 fixed on the base 63. Seals 77 are provided between the hood and the seat. The seat 75 comprises on the back two passages 79 for the inlet and outlet of conditioned air or other gas. The displacement sensors 35 are mounted in a ruler 81 fixed on the base 63 and coupled to electronic circuits accommodated under the base. The posts 55 and 57 are provided with a friction and adjustment plate 82 at the positions where the lower portion of frame 51 abuts against these posts.

Figure 4:
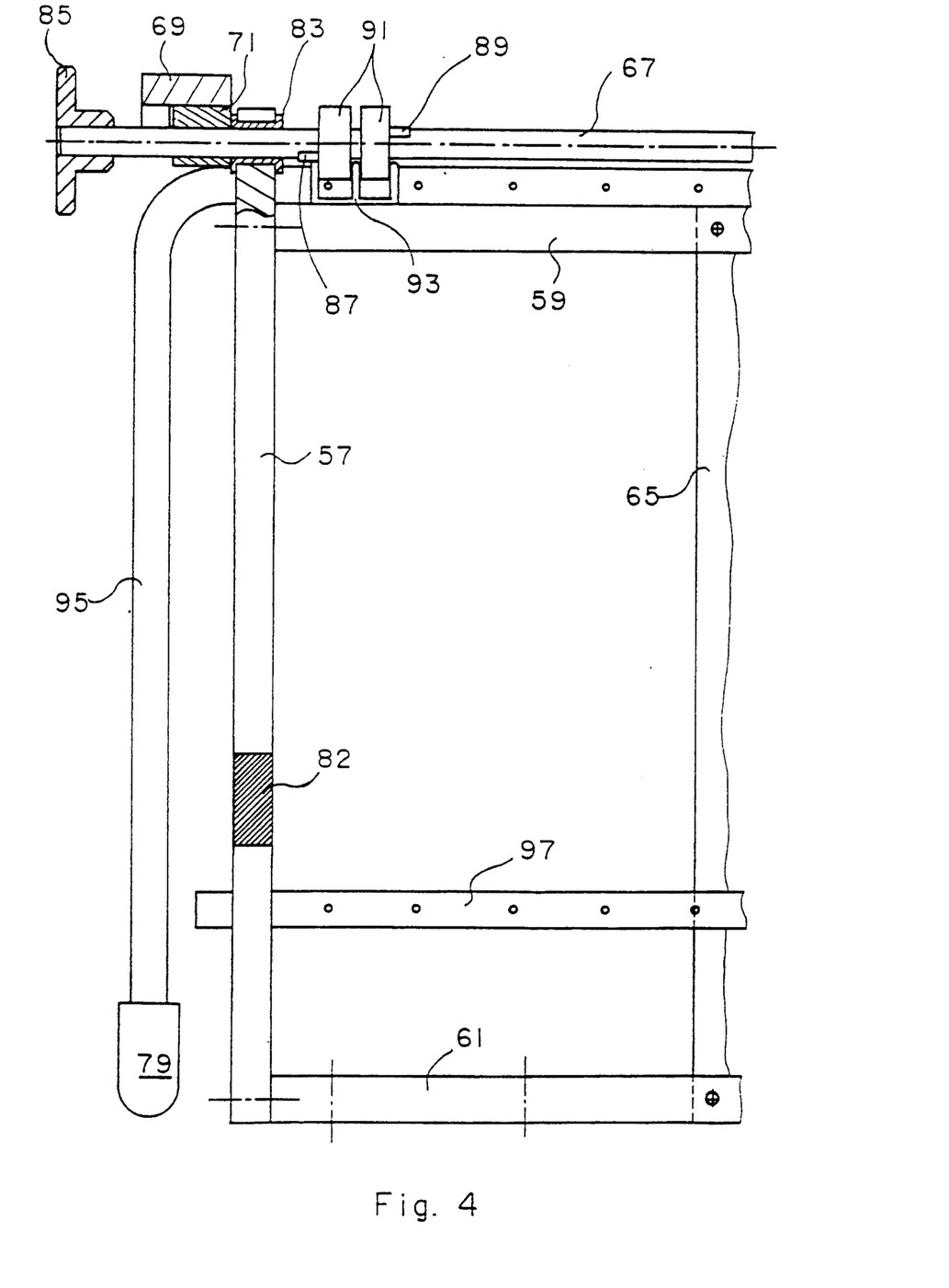
FIG. 4 shows a partial front view of the frame of the apparatus of FIGS. 3A and 3B.

FIG. 4 shows a partial front view of the apparatus frame. Axis 67 passes in bearings 83 of the posts 55 and 57 and comprises at its extremities rollers 85 enabling an operator to position frame 51 to its normal low or high position. The high position is useful to calibrate the sensors, the calibration being made by removing the frame from its normal position to the high position and by checking whether the values indicated by a measurement acquisition system connected to the electronic circuits of the sensors correspond to the displacement which is known with accuracy. If the values indicated do not coincide, the measurement acquisition system is readjusted.

The high and low positions are obtained with eccentrics 71 which are urged, as shown, against a horizontal portion of supports 69. The rotation of eccentrics 71 corresponding to these two positions is determined by two abutments 87 and 89 axially mounted in disks 91 integral with axis 67. Abutments 87 and 89 are respectively urged against the front and rear surfaces of a part 93 mounted on the upper spacer 59.

A passage 79 for the inlet or outlet of the conditioned air is coupled to a tube 95. Tube 95 rises to the upper part of the apparatus where it horizontally extends and where it comprises apertures. A tube 97 coupled to the other passage (not shown) comprises, at the lower part of the apparatus, a pierced horizontal portion.

Figure 5:
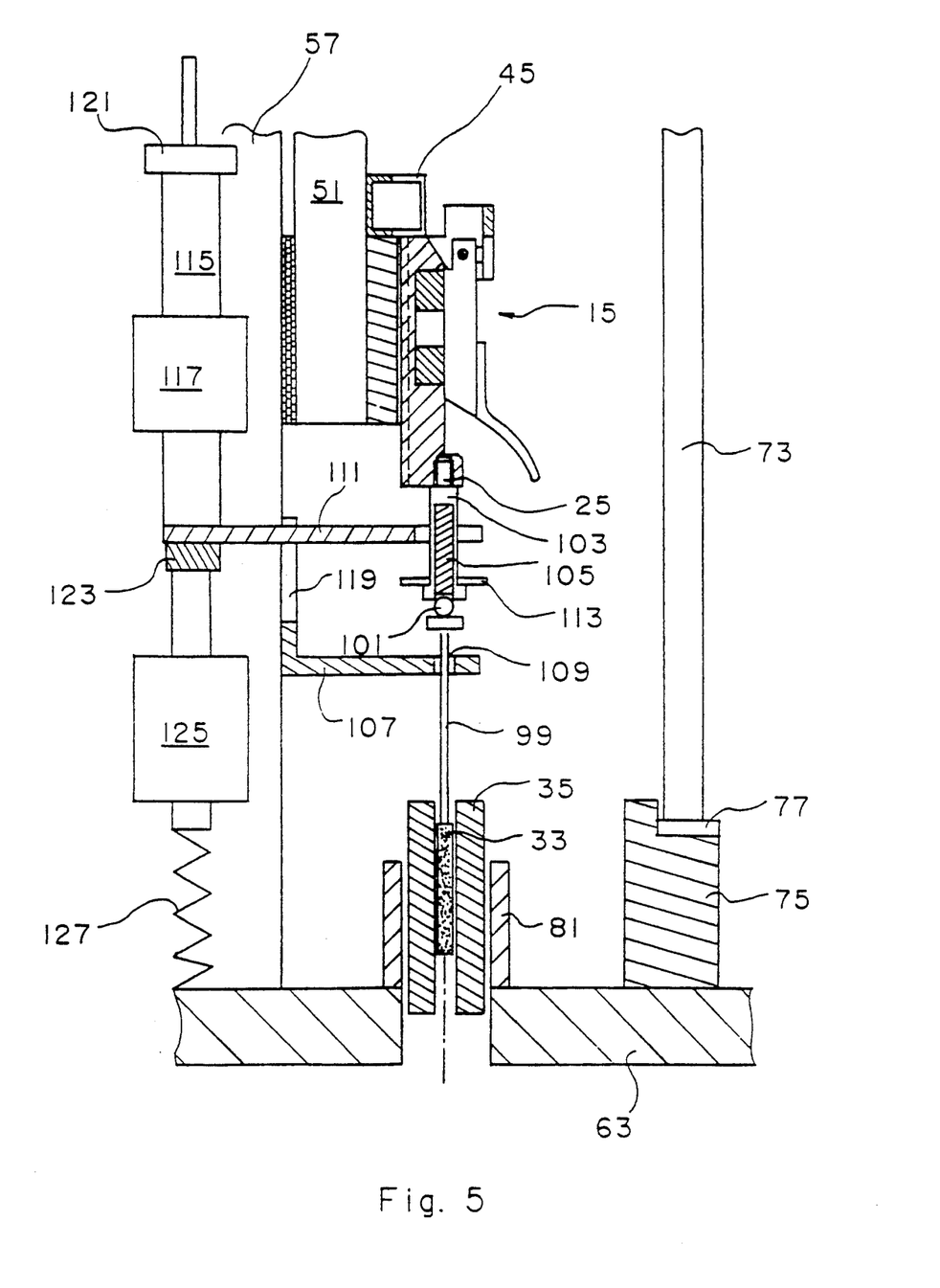
FIG. 5 illustrates a fastening means for a low gripping jaw to a displacement sensor and schematically shows a device to increase the elongation of sample strips.

FIG. 5 represents in more detail the fastening of a lower gripping jaw 15 to its corresponding displacement sensor 35, and schematically an additional ballasting device for the sample strips.

Fastening of the gripping jaw to the sensor is achieved by a magnetic gripping device. At the end of a rod 99 connected to the solenoid plunger 33 of sensor 35 is fixed a ball 101 made of a ferromagnetic material. A hollow vertical cylinder 103 made of a non-magnetic material is screwed in the inside thread 25 of the gripping jaw. In the cylinder 103 is accommodated a magnet 105 flush with the lower portion of the cylinder. Thus, when it is desired to fasten the solenoid plunger 33 to the gripping jaw 15, it is simply necessary to draw cylinder 103 near ball 101, or reversely, and the latter is urged against the lower portion of the cylinder while being centered in the internal portion of the cylinder.

Such a gripping device has several advantages. The assembly of ball 101 urged against its cylinder 103 is a pivot coupling which ensures a satisfactory centering of the solenoid plunger 33 in sensor 35. The magnetic attraction can be high enough so that, during the insertion of a strip, above described, the lower gripping jaw 15 gets coupled to its sensor without being acted upon during insertion. The absence of mechanical coupling ensures simple handling and protection of the fragile sensors 35, especially of rods 99 and solenoid plungers 33, when, for example, frame 51 is removed without previously removing the gripping jaws 15 from the sensors.

A bracket 107 fixed on posts 55 and 57 comprises vertical holes 109 in which pass the rods 99 of sensors 35. Each rod 99 comprises at its upper portion a shoulder which prevents the rod from falling through the corresponding hole 109. In order to remove the gripping jaws 15 from the sensors, it is possible to manually separate the balls by pulling the rods 99 downwardly. It is also possible to slightly tilt the frame 51 about axis 67, the rods 99 will then be retained in holes 109 and balls 101 will be separated by the movement of the frame.

The apparatus further comprises an additional ballasting device for the sample strips serving to determine, for example, the elastic modulus of each of the strips under various humidity conditions. This device comprises for each strip, a horizontal fork 111 which, when it is desired to further load the strip, abuts against a shim ring 113 of cylinder 103. The fork 111 is fixed to the lower end of a vertical axis 115 sliding along a ball socket 117 fixed to the frame and serving as a load. The fork 111 is guided by a vertical groove 119 of the bracket 107. At the upper portion of axes 115, it is possible to add additional ballasts 121. The lower portions of axes 115 lay on a horizontal ruler 123 which is fixed to the upper piston portion of two double action cylinders 125 (one cylinder can be seen in FIG. 5). In standby position, the pistons of cylinders 125 are maintained in a high position where the fork 111 does not contact the shim rings 113, by two springs 127 abutting between the lower portions of the pistons of the cylinders and the base 63. When it is desired to load the sample strips, cylinders 125 are activated, their pistons are lowered while pressing on springs 127, the forks 111 are freed and abut against the shim rings 113 while increasing the elongation of the strips.

The apparatus according to the invention is provided to be used with an air source at a humidity degree electronically regulated developed by the applicant. Thus, the whole apparatus according to the invention and the air source can be entirely controlled by computer, which adjusts the humidity degree in the chamber by stages maintained for a sufficient period, storing the indications of the displacement sensors while determining elongations and, if necessary, actuating cylinders 125 to add additional loads to the sample strips and to determine the elastic modulus of the strips according to their additional elongations.

As is apparent to those skilled in the art, various variants and modifications can be made to the above disclosed apparatus for measuring elongation. For example, the apparatus can be provided with conventional gripping jaws provided with clips or eccentrics. The various elements that are not devised for being dismounted can be welded instead of being screwed. The apparatus can be used for any type of strips with different types of atmosphere.

I claim:

1. An apparatus for measuring the respective elongations of several sample strips (13), comprising a base (63), a vertical frame (51), and for each strip:

a fixed upper gripping jaw (27) to tighten the upper extremity of the strip;
 a mobile lower gripping jaw (15) to tighten the lower extremity of the strip and to stretch it by gravity effect; and
 a displacement sensor for the lower gripping jaw;
 wherein the gripping jaws are magnetic gripping jaws, each of which comprises a sole (1) and a plate (3) articulated on the sole, a magnet (11) being mounted in the sole to urge the plate against the sole by magnetic attraction, the soles of the lower gripping jaws being guided vertically with respect to the frame.

2. An apparatus according to claim 1, wherein the sole (1) of each lower gripping jaw (15) is made of a non-magnetic material and wherein the gripping jaw is guided by a groove (29) achieved in a piece made of a ferromagnetic material fixed to said frame (51), the gripping jaw being maintained and guided in said groove only by the attraction of its magnet.

3. An apparatus according to claim 1, wherein each lower gripping jaw (15) is coupled to the corresponding displacement sensor (33, 35) by a magnetic gripping means.

4. An apparatus according to claim 1, wherein each gripping jaw comprises an articulation (7, 9) of said plate (3) on the sole (1) having a clearance perpendicular to said contact surface.

5. An apparatus according to claim 1, wherein the sole (1) of each gripping jaw comprises lateral walls (5) for guiding the strip to be tightened.

6. An apparatus according to claim 1, wherein said displacement sensors are solenoid plunger sensors (33) including a displacement sensor (35), said solenoid plungers being coupled to said corresponding lower gripping jaws (15).

7. An apparatus according to claim 1, comprising means for increasing the elongation of said strips by addition of loads on said lower gripping jaws (15).

8. An apparatus according to claim 1, wherein said displacement sensors are fixed to said base (63), said apparatus comprising means (71) for positioning said frame (51) to high and low positions with respect to said base.

9. An apparatus according to claim 1, comprising a horizontal ruler (45) disposed between said upper (27) and lower (15) gripping jaws, said ruler having a lateral position where said lower gripping jaws (15) freely slide along the vertical direction and another position where said lower gripping jaws abut against said ruler.

* * * * *